(12) United States Patent
Gao et al.

(10) Patent No.: US 9,895,686 B2
(45) Date of Patent: Feb. 20, 2018

(54) DOUBLE-COMPONENT MODIFIED MOLECULAR SIEVE WITH IMPROVED HYDROTHERMAL STABILITY AND PRODUCTION METHOD THEREOF

(75) Inventors: Xionghou Gao, Lanzhou (CN); Dong Ji, Lanzhou (CN); Haitao Zhang, Lanzhou (CN); Hongchang Duan, Lanzhou (CN); Di Li, Lanzhou (CN); ZhengGuo Tan, Lanzhou (CN); Yi Su, Lanzhou (CN); Zhicheng Tang, Lanzhou (CN); Yi Wang, Lanzhou (CN); Yanqing Ma, Lanzhou (CN); Yanbo Sun, Lanzhou (CN)

(73) Assignee: PetroChina Company Limited, Beijing Dongcheng District (CN)

( * ) Notice: Subject to any disclaimer, the term of this patent is extended or adjusted under 35 U.S.C. 154(b) by 1167 days.

(21) Appl. No.: 13/505,219

(22) PCT Filed: Dec. 1, 2009

(86) PCT No.: PCT/CN2009/001353
§ 371 (c)(1),
(2), (4) Date: Jul. 16, 2012

(87) PCT Pub. No.: WO2011/050505
PCT Pub. Date: May 5, 2011

(65) Prior Publication Data
US 2012/0275994 A1    Nov. 1, 2012

(30) Foreign Application Priority Data

Oct. 30, 2009   (CN) .......................... 2009 1 0237007

(51) Int. Cl.
| | | |
|---|---|---|
| *B01J 29/06* | (2006.01) | |
| *B01J 37/28* | (2006.01) | |
| *B01J 29/04* | (2006.01) | |
| *B01J 29/12* | (2006.01) | |
| *B01J 29/068* | (2006.01) | |
| *B01J 29/44* | (2006.01) | |
| *B01J 29/74* | (2006.01) | |
| *C01B 39/02* | (2006.01) | |
| *C07C 4/06* | (2006.01) | |
| *C10G 11/18* | (2006.01) | |
| *B01J 37/02* | (2006.01) | |
| *B01J 37/08* | (2006.01) | |

(52) U.S. Cl.
CPC ............. *B01J 37/28* (2013.01); *B01J 29/041* (2013.01); *B01J 29/061* (2013.01); *B01J 29/068* (2013.01); *B01J 29/126* (2013.01); *B01J 29/44* (2013.01); *B01J 29/7415* (2013.01); *B01J 37/0207* (2013.01); *C01B 39/026* (2013.01); *C07C 4/06* (2013.01); *C10G 11/18* (2013.01); *B01J 37/0236* (2013.01); *B01J 37/08* (2013.01); *B01J 2229/186* (2013.01); *B01J 2229/24* (2013.01); *B01J 2229/37* (2013.01); *B01J 2229/40* (2013.01); *C07C 2529/12* (2013.01); *C07C 2529/22* (2013.01); *C07C 2529/44* (2013.01); *C07C 2529/74* (2013.01); *C10G 2300/1044* (2013.01); *C10G 2400/20* (2013.01)

(58) Field of Classification Search
USPC ......................................... 502/60, 77, 79, 85
See application file for complete search history.

(56) References Cited

U.S. PATENT DOCUMENTS

| | | | |
|---|---|---|---|
| 3,702,886 A | 11/1972 | Argauer et al. | |
| 3,965,208 A | 6/1976 | Butter et al. | |
| 3,972,383 A | 8/1976 | Green | |
| 4,276,438 A * | 6/1981 | Chu ........................ | B01J 29/44 585/466 |
| 4,399,059 A | 8/1983 | Chu | |

(Continued)

FOREIGN PATENT DOCUMENTS

| | | |
|---|---|---|
| CN | 85102828 A | 7/1986 |
| CN | 1072031 C | 3/1999 |

(Continued)

OTHER PUBLICATIONS

Dong Ji et al., Machine Translation of CN 101537365, 2009.*

(Continued)

*Primary Examiner* — Elizabeth Wood
(74) *Attorney, Agent, or Firm* — Schwegman Lundberg & Woessner, P.A.

(57) ABSTRACT

A method for producing double-component modified molecular sieve comprises adding molecular sieve to an aqueous solution containing phosphorus to form a mixture, allowing the mixture to react at pH of 1-10, temperature of 70-200° C. and pressure of 0.2-1.2 MPa for 10-200 min, and then filtering, drying and baking the resultant to obtain phosphorus-modified molecular sieve, and then adding the phosphorus-modified molecular sieve to an aqueous solution containing silver ions, allowing the phosphorus-modified molecular sieve to react with silver ions at 0-100° C. in dark condition for 30-150 min, and then filtering, drying and baking. The obtained double-component modified molecular sieve contains 88-99 wt % molecular sieve with a ratio of silica to alumina between 15 and 60, 0.5-10 wt % phosphorus (based on oxides) and 0.01-2 wt % silver (based on oxides), all based on dry matter. A catalyst produced from the double-component modified molecular sieve has improved hydrothermal stability and microactivity.

1 Claim, No Drawings

(56) References Cited

U.S. PATENT DOCUMENTS

| | | | |
|---|---|---|---|
| 4,845,063 A | | 7/1989 | Chu |
| 5,171,921 A | | 12/1992 | Gaffney et al. |
| 5,968,342 A | * | 10/1999 | Tsunoda .................. B01J 29/068 208/113 |
| 5,997,728 A | | 12/1999 | Adewuyi et al. |
| 6,307,117 B1 | * | 10/2001 | Tsunoda et al. .............. 585/651 |

FOREIGN PATENT DOCUMENTS

| | | | |
|---|---|---|---|
| CN | 1072032 C | | 3/1999 |
| CN | 1211469 A | | 3/1999 |
| CN | 1211470 A | | 3/1999 |
| CN | 1217231 A | | 5/1999 |
| CN | 1245087 A | | 2/2000 |
| CN | 1317543 A | | 10/2001 |
| CN | 1721505 A | | 1/2006 |
| CN | 1872415 A | | 12/2006 |
| CN | 101537365 | * | 9/2009 |
| CN | 101537365 A | | 9/2009 |
| EP | 0603900 B1 | * | 7/1998 |
| WO | WO-2011/050505 | | 5/2011 |
| WO | WO-2014116801 | | 7/2014 |

OTHER PUBLICATIONS

Hongzhou et al., Machine translation of CN 1317543, Oct. 2001.*
"International Application No. PCT/CN2009/001353, International Search Report dated Aug. 12, 2010", (Aug. 12, 2010), 10 pgs.
"Canadian Application No. 2,779,312, Office Action dated Oct. 27, 2015", (Oct. 27, 2015), 5 pgs.

* cited by examiner

DOUBLE-COMPONENT MODIFIED MOLECULAR SIEVE WITH IMPROVED HYDROTHERMAL STABILITY AND PRODUCTION METHOD THEREOF

PRIORITY CLAIM TO RELATED APPLICATIONS

This application is a national stage application under 35 U.S.C. § 371 of PCT/CN2009/001353, filed Dec. 1, 2009, and published as WO 2011/050505 A1 on May 5, 2011, which claims priority to Chinese Application No. 200910237007.4, filed Oct. 30, 2009, which applications and publication are incorporated herein by reference and made a part hereof in their entirety, and the benefit of priority of each of which is claimed herein.

TECHNICAL FIELD OF THE INVENTION

The present invention belongs to the technical field of molecular sieve modification, and in particular relates to a double-component modified molecular sieve with improved hydrothermal stability and the preparation method thereof.

BACKGROUND ART OF THE INVENTION

In recent years, the domestic and international researchers and producers in the field of refining catalysts has devoted themselves to improve the performance of FCC catalyst by means of molecular sieves with various types of structure in order to increase the yields of light olefins in FCC plants. This is because the primary process for traditional production of ethylene and propylene, i.e. steam pyrolysis, is performed by the free radical reactions, wherein the temperature is high and the requirement to feedstock is rigorous. In contrast, catalytic pyrolysis for producing light olefins has relatively lower cost and is the hot spot in the domestic and international research for increasing light olefin capacity. Functionalized shape-selective molecular sieves deserve wide attention as the major active constituent in such kind of catalytic converting catalyst.

Since USA Mobil Company has developed the ZSM-5 zeolite molecular sieve (U.S. Pat. No. 3,702,886) in 1972, it has been widely applied in petrochemical processes, such as shape-selective cracking (CN 1872415A), alkylation, isomerisation, disproportionation, catalytic dewaxing, etherification and etc. of hydrocarbons, due to its properties of relatively high silica to alumina ratio, unique pore structure, and excellent thermal and hydrothermal stabilities. In particular, adding ZSM-5 zeolite into normal catalysts or aids for catalytic cracking enables to significantly increase the yields of light olefins and the octane number (U.S. Pat. No. 5,997,728).

However, the ZSM-5 zeolite molecular sieve is readily to be deactivated under the hydrothermal condition of the catalytic cracking, and thus the stability and selectivity are both affected. Therefore, a number of researches have been carried out about the modification to the ZSM-5 zeolite molecular sieve.

In U.S. Pat. No. 4,399,059, diammonium hydrogen phosphate or ammonium dihydrogen phosphate is mixed with $NH_4$-ZSM-5 and dried, and the mixture is calcined at 500° C. so as to produce a phosphorus-modified ZSM-5 zeolite, which makes it possible to significantly improve the selectivity of para isomer product when used in the isomerisation reaction of xylene.

U.S. Pat. No. 5,171,921 discloses a ZSM-5 molecular sieve modified by impregnating with phosphorus compounds. Such modified molecular sieve may be used as the catalytically active constituent that converts olefins or aliphatic hydrocarbons into $C_2$-$C_5$ olefins.

U.S. Pat. No. 3,972,382 and U.S. Pat. No. 3,965,208 disclose that the reaction selectivity of the HZSM-5 is improved after being modified with trimethyl phosphite.

CN 85102828 reports modifying the ZSM-5 molecular sieve using a method by impregnating and evaporating, and the phosphorus-modified molecular sieve has a substantially improved activity in the shape-selective catalysis for preparing para-ethyltoluene by alkylation of toluene with ethylene.

CN 97120271 reports a phosphorus-containing faujasite as hydrocarbon cracking catalyst, said phosphorus-containing faujasite is prepared by uniformly mixing faujasite with an aqueous solution of a phosphorus-containing compound followed by drying and calcining at 450-600° C. for more than 0.5 h, and has a relatively good catalytic activity.

CN 98117286 reports a phosphorous zeolite comprising 90-99.9 wt % of aluminosilicate zeolite and 0.1-10 wt % of phosphorus based on $P_2O_5$, which has higher hydrocarbon converting activity, higher diesel selectivity, and better resistance to vanadium, nickel and other heavy metal.

CN 1211469A and CN 1211470A report a molecular sieve composition with increased yields of propylene and ethylene, characterized in that, it is obtained by adding a five-membered ring molecular sieve into an aqueous solution of a compound comprising phosphorus and alkaline earth metal ions and/or transition metal ions, mixing until homogeneous, and allowing impregnation reaction, said composition is composed by 85-95 wt % of five-membered ring molecular sieve, 2-10 wt % of phosphorus based on oxide, 0.3-5 wt % of alkaline earth metal based on oxide, 0.3-5 wt % of transition metal element based on oxide.

CN 1072031C and CN 1072032C also report a five-membered ring molecular sieve composition with increased yields of propylene and ethylene(especially ethylene), which is composed by 88-95 wt % of five-membered ring molecular sieve, 2-8 wt % of phosphorus based on oxide, 0.3-3 wt % of alkaline earth metal based on oxide, 0-3 wt % of transition metal element based on oxide. The preparation method of said composition is one step impregnation method, wherein the procedure is not only relatively simple and well reliable, but also has a substantially increased ethylene yield.

The yields of light olefins, in particular propylene, of the catalytic cracking catalysts used in the industry in prior art are not sufficient to satisfy the practical requirement of the manufactures of refining and chemical engineering. Therefore, it is quite meaningful to substantially increase propylene yield. So far it seems that modification to the functionalized shape-selective molecular sieve would be the most efficient route to increase the yields of light olefins in catalytic cracking.

However, when a second modifying constituent is introduced into the traditional phosphorus-modified molecular sieve via ion exchange, the phosphorus element in the molecular sieve would be largely washed away, and thus the purpose of modifying the molecular sieve with two components can not be achieved. As a result, the stability and catalytic activity of the molecular sieve are affected.

SUMMARY OF THE INVENTION

The purpose of the present invention consists in, with regards to the current molecular sieve materials and technologies, providing a double-component modified molecular sieve with substantially improved hydrothermal stability and the preparation method thereof.

A method for preparing double-component modified molecular sieves with improved hydrothermal stability, wherein a molecular sieve is added into an aqueous solution containing phosphorus followed by filtering, drying and calcining, characterized in that, according to said method, the molecular sieve is added to an aqueous solution containing phosphorus and allowed to react at pH of 1-10 (preferably 2-7) at a reaction temperature of 70-200° C. (preferably 90-160° C.) under a reaction pressure of 0.2-1.2 MPa (preferably 0.2-0.8 MPa) for 10-200 minutes, followed by filtering, drying and calcining, so as to obtain a phosphorus-modified molecular sieve; the phosphorus-modified molecular sieve is added into an aqueous solution containing silver ions and allowed to react in dark place at reaction temperature of 0-100° C. (preferably 20-60° C.) for 30-150 minutes, followed by filtering, drying and calcining, so as to obtain a double-component modified molecular sieve.

In the method provided by the present invention, the filtering, drying and calcining during the modification all employ the processes and technical parameters that are commonly used in prior art, in another words, there is no particular limitation in the present invention, and it is recommended that the drying temperature is in the range of 100-120° C., the calcining temperature is in the range of 200-800° C. and the calcining time is in the range of 0.5-10 h.

The modification condition of the present invention differs from that of the conventional phosphorus modification method, and consists in high temperature while a certain pressure is involved. The diffusion of modifying constituents in pores of the molecular sieve can be further enhanced by the synergy of the high temperature and of pressurization, which enables the modifying constituents to enter deeper pores within the molecular sieve and react with the B acid sites on the surface thereof. Such a satisfying effect can not be achieved when the high temperature is solely applied without pressurization or else the pressurization is carried out at low temperature. Water is also necessary, of course, as the medium.

There is no particular limitation for the aqueous solution containing phosphorus in the method provided by the present invention, and any phosphorus-containing aqueous solution that may be used for phosphorus modification of molecular sieves is appropriate. There is either no particular limitation for the phosphorous compound in the phosphorus-containing aqueous solution except for being able to dissolve in water. For example, the aqueous solution containing phosphorus may be one or more of a solution of phosphoric acid, a solution of phosphorous acid, an aqueous solution of a soluble phosphate, an aqueous solution of a soluble phosphite and etc. The aqueous solution of a soluble phosphate or of a soluble phosphite may be the aqueous solution of a phosphate or a phosphite such as triammonium phosphate, diammonium hydrogen phosphate, ammonium dihydrogen phosphate and so on. The weight ratio of the aqueous solution containing phosphorus to the molecular sieve is preferably in the range from 2:1 to 5:1.

The aqueous solution containing silver ions in accordance with the present application may be an aqueous solution of silver nitrate, silver acetate or the mixture thereof. The weight ratio of the aqueous solution containing silver ions to the molecular sieve is preferably in the range from 2:1 to 10:1, and the aqueous solution containing silver ions has a preferable concentration of 0.01-0.1 mol/L.

It is not necessary for the present invention to specialize the type of the molecular sieve used in the method or the composition thereof, the form of phosphorus or the form of silver, that is, it depends on the requirement. The molecular sieve is preferably one of ZSM type, 13 type, Y type and MCM type molecular sieve, more preferably one of ZSM type and 13 type molecular sieve, with a silica to alumina ratio in the range of 15-100, preferably 15-60.

The present invention also claims a modified molecular sieve produced by using the modification method in accordance with the present invention, and provides an optimal modified molecular sieve produced by using the modification method in accordance with the present invention, which contains, based on dry basis, 88-99 wt % of a molecular sieve with a silica to alumina ratio of 15-60, 0.5-10 wt % of phosphorus based on oxide and 0.01-2 wt % of silver based on oxide. Said double-component modified molecular sieve has excellent hydrothermal stability and activity.

DETAILED DESCRIPTION OF THE INVENTION

The analysis methods in each examples and comparative examples are as follows:

1. The element analysis is measured by X-ray fluorescence spectrometry (XRF), wherein the instrument used is Japanese Rigaku "ZSX primus" type X-ray fluorescence spectrometer.

2. The stability is evaluated by the difference between the relative crystallinity (ZSM-5%) before and after hydrothermal aging at 800° C. for 4 h and that at 800° C. for 17 h, wherein the crystallinity is measured on a X-ray diffractomer D/max-3C from Japanese Rigaku Company.

3. The activity is evaluated on a microreactor apparatus sold by Huayang Company, Beijing. The feedstock oil is light diesel oil from Dagang. The evaluation condition is as follows: the catalyst is treated by 100% water steam at 800° C. for 4 h or 17 h; the load of the catalyst is 5 g; the reaction temperature is 460° C.; the reaction time is 70 s; and the catalyst/oil ratio is 3.2.

Example 1

9.3 g of $(NH_4)_2HPO_4$ is dissolved in 500 g of distilled water. 100 g of ZSM-5 molecular sieve sample is added to the solution under stirring, and pH value is adjusted to 4. The mixture is stirred and allowed to react at reaction temperature of 100° C. under reaction pressure of 0.2 MPa for 60 min, followed by filtering and drying, and then calcined at 500° C. for 4 h. The molecular sieve sample thus obtained is labeled as PZ-1.

0.73 g of $AgNO_3$ is dissolved in 350 g of distilled water. The molecular sieve PZ-1 is added to the silver-containing solution. The mixture is stirred and allowed to react in dark place at reaction temperature of 20° C. for 120 min, followed by filtering and drying, and then calcined at 500° C. for 2 h, so as to obtain a double-component modified molecular sieve APZ-1. Subsequently, kaolin (45%), alumina gel (15%) and APZ-1 (40%) are added into distilled water in the above proportion under slurrying, dried at 120° C. and calcined at 450° C. for 1 h, followed by crushing and screening. The catalyst sample thus obtained is labeled as C-1, from which 20-40 mesh catalyst particles are tested for their activity in the microreactor. Tables 1-3 show the composition of the sample, the crystallinity before and after aging, and the activity of this model catalyst tested in the microreactor.

Example 2

18.6 g of $(NH_4)_2HPO_4$ is dissolved in 400 g of distilled water. 100 g of ZSM-5 molecular sieve sample is added to the solution under stirring, and pH value is adjusted to 3. The mixture is stirred and allowed to react at reaction temperature of 120° C. under reaction pressure of 0.4 MPa for 120 min, followed by filtering and drying, and then calcined at 550° C. for 4 h. The molecular sieve sample thus obtained is labeled as PZ-2.

1.46 g of $AgNO_3$ is dissolved in 350 g of distilled water. The molecular sieve PZ-2 is added to the silver-containing solution. The mixture is stirred and allowed to react in dark place at reaction temperature of 40° C. for 100 min, followed by filtering and drying, and then calcined at 500° C. for 2 h, so as to obtain a double-component modified molecular sieve APZ-2. Subsequently, kaolin (45%), alumina gel (15%) and APZ-2 (40%) are added into distilled water in fixed proportion under slurrying, dried at 120° C. and calcined at 450° C. for 1 h, followed by crushing and screening. The catalyst sample thus obtained is labeled as C-2, from which 20-40 mesh catalyst particles are tested for their activity in the microreactor. Tables 1-3 show the composition of the sample, the crystallinity before and after aging, and the activity of this model catalyst tested in the microreactor.

Example 3

37.2 g of $(NH_4)_2HPO_4$ is dissolved in 500 g of distilled water. 100 g of ZSM-5 molecular sieve sample is added to the solution under stirring, and pH value is adjusted to 2. The mixture is stirred and allowed to react at reaction temperature of 140° C. under reaction pressure of 1 MPa for 200 min, followed by filtering and drying, and then calcined at 450° C. for 6 h. The molecular sieve sample thus obtained is labeled as PZ-3.

2.19 g of $AgNO_3$ is dissolved in 400 g of distilled water. The molecular sieve PZ-3 is added to the silver-containing solution. The mixture is stirred and allowed to react in dark place at reaction temperature of 60° C. for 60 min, followed by filtering and drying, and then calcined at 500° C. for 2 h, so as to obtain a double-component modified molecular sieve APZ-3. Subsequently, kaolin (45%), alumina gel (15%) and APZ-3 (40%) are added into distilled water in fixed proportion under slurrying, dried at 120° C. and calcined at 450° C. for 1 h, followed by crushing and screening. The catalyst sample thus obtained is labeled as C-3, from which 20-40 mesh catalyst particles are tested for their activity in the microreactor. Tables 1-3 show the composition of the sample, the crystallinity before and after aging, and the activity of this model catalyst tested in the microreactor.

Example 4

25.1 g of $(NH_4)_2HPO_4$ is dissolved in 500 g of distilled water. 100 g of ZSM-5 molecular sieve sample is added to the solution under stirring, and pH value is adjusted to 3. The mixture is stirred and allowed to react at reaction temperature of 140° C. under reaction pressure of 0.4 MPa for 200 min, followed by filtering and drying, and then calcined at 550° C. for 4 h. The molecular sieve sample thus obtained is labeled as PZ-4.

2.19 g of AgAc is dissolved in 400 g of distilled water. The molecular sieve PZ-4 is added to the silver-containing solution. The mixture is stirred and allowed to react in dark place at reaction temperature of 20° C. for 300 min, followed by filtering and drying, and then calcined at 500° C. for 2 h, so as to obtain a double-component modified molecular sieve APZ-4. Subsequently, kaolin (45%), alumina gel (15%) and APZ-4 (40%) are added into distilled water in fixed proportion under slurrying, dried at 120° C. and calcined at 450° C. for 1 h, followed by crushing and screening. The catalyst sample thus obtained is labeled as C-4, from which 20-40 mesh catalyst particles are tested for their activity in the microreactor. Tables 1-3 show the composition of the sample, the crystallinity before and after aging, and the activity of this model catalyst tested in the microreactor.

Example 5

16.2 g of $NH_4H_2PO_4$ is dissolved in 250 g of distilled water. 100 g of ZSM-5 molecular sieve sample is added to the solution under stirring, and pH value is adjusted to 2. The mixture is stirred and allowed to react at reaction temperature of 120° C. under reaction pressure of 0.4 MPa for 60 min, followed by filtering and drying, and then calcined at 600° C. for 2 h. The molecular sieve sample thus obtained is labeled as PZ-5.

1.46 g of $AgNO_3$ is dissolved in 300 g of distilled water. The molecular sieve PZ-5 is added to the silver-containing solution. The mixture is stirred and allowed to react in dark place at reaction temperature of 20° C. for 200 min, followed by filtering and drying, and then calcined at 500° C. for 2 h, so as to obtain a double-component modified molecular sieve APZ-5. Subsequently, kaolin (45%), alumina gel (15%) and APZ-5 (40%) are added into distilled water in fixed proportion under slurrying, dried at 120° C. and calcined at 450° C. for 1 h, followed by crushing and screening. The catalyst sample thus obtained is labeled as C-5, from which 20-40 mesh catalyst particles are tested for their activity in the microreactor. Tables 1-3 show the composition of the sample, the crystallinity before and after aging, and the activity of this model catalyst tested in the microreactor.

Example 6

28.2 g of $NH_4H_2PO_4$ is dissolved in 500 g of distilled water. 100 g of ZSM-5 molecular sieve sample is added to the solution under stirring, and pH value is adjusted to 2. The mixture is stirred and allowed to react at reaction temperature of 130° C. under reaction pressure of 0.6 MPa for 120 min, followed by filtering and drying, and then calcined at 600° C. for 2 h. The molecular sieve sample thus obtained is labeled as PZ-6.

2.19 g of AgAc is dissolved in 300 g of distilled water. The molecular sieve PZ-6 is added to the silver-containing solution. The mixture is stirred and allowed to react in dark place at reaction temperature of 60° C. for 300 min, followed by filtering and drying, and then calcined at 500° C. for 2 h, so as to obtain a double-component modified molecular sieve APZ-6. Subsequently, kaolin (45%), alumina gel (15%) and APZ-6 (40%) are added into distilled water in fixed proportion under slurrying, dried at 120° C. and calcined at 450° C. for 1 h, followed by crushing and screening. The catalyst sample thus obtained is labeled as C-6, from which 20-40 mesh catalyst particles are tested for their activity in the microreactor. Tables 1-3 show the composition of the sample, the crystallinity before and after aging, and the activity of this model catalyst tested in the microreactor.

Example 7

16.2 g of $H_3PO_4$ is dissolved in 200 g of distilled water. 100 g of ZSM-5 molecular sieve sample is added to the solution under stirring, and pH value is adjusted to 2. The mixture is stirred and allowed to react at reaction temperature of 200° C. under reaction pressure of 1.0 MPa for 60 min, followed by filtering and drying, and then calcined at 450° C. for 6 h. The molecular sieve sample thus obtained is labeled as PZ-7.

1.46 g of $AgNO_3$ is dissolved in 400 g of distilled water. The molecular sieve PZ-7 is added to the silver-containing solution. The mixture is stirred and allowed to react in dark place at reaction temperature of 40° C. for 240 min, followed by filtering and drying, and then calcined at 500° C. for 2 h, so as to obtain a double-component modified molecular sieve APZ-7. Subsequently, kaolin (45%), alumina gel (15%) and APZ-7 (40%) are added into distilled water in fixed proportion under slurrying, dried at 120° C. and calcined at 450° C. for 1 h, followed by crushing and screening. The catalyst sample thus obtained is labeled as C-7, from which 20-40 mesh catalyst particles are tested for their activity in the microreactor. Tables 1-3 show the composition of the sample, the crystallinity before and after aging, and the activity of this model catalyst tested in the microreactor.

Example 8

28.2 g of $H_3PO_4$ is dissolved in 400 g of distilled water. 100 g of ZSM-5 molecular sieve sample is added to the solution under stirring, and pH value is adjusted to 2. The mixture is stirred and allowed to react at reaction temperature of 120° C. under reaction pressure of 0.6 MPa for 200 min, followed by filtering and drying, and then calcined at 600° C. for 2 h. The molecular sieve sample thus obtained is labeled as PZ-8.

1.09 g of AgAc and 1.07 g of $AgNO_3$ are dissolved in 400 g of distilled water. The molecular sieve PZ-8 is added to the silver-containing solution. The mixture is stirred and allowed to react in dark place at reaction temperature of 60° C. for 300 min, followed by filtering and drying, and then calcined at 500° C. for 2 h, so as to obtain a double-component modified molecular sieve APZ-8. Subsequently, kaolin (45%), alumina gel (15%) and APZ-8 (40%) are added into distilled water in fixed proportion under slurrying, dried at 120° C. and calcined at 450° C. for 1 h, followed by crushing and screening. The catalyst sample thus obtained is labeled as C-8, from which 20-40 mesh catalyst particles are tested for their activity in the microreactor. Tables 1-3 show the composition of the sample, the crystallinity before and after aging, and the activity of this model catalyst tested in the microreactor.

Example 9

9.3 g of $(NH_4)_2HPO_4$ is dissolved in 100 g of distilled water. 100 g of β molecular sieve sample is added to the solution under stirring, and pH value is adjusted to 4. The mixture is stirred and allowed to react at reaction temperature of 110° C. under reaction pressure of 0.4 MPa for 120 min, followed by filtering and drying, and then calcined at 500° C. for 6 h. The molecular sieve sample thus obtained is labeled as Pβ-1.

0.73 g of $AgNO_3$ is dissolved in 300 g of distilled water. The molecular sieve Pβ-1 is added to the silver-containing solution. The mixture is stirred and allowed to react in dark place at reaction temperature of 20° C. for 100 min, followed by filtering and drying, and then calcined at 500° C. for 2 h, so as to obtain a double-component modified molecular sieve Aβ-1. Subsequently, kaolin (45%), alumina gel (15%) and APβ-1 (40%) are added into distilled water in fixed proportion under slurrying, dried at 120° C. and calcined at 500° C. for 1 h, followed by crushing and screening. The catalyst sample thus obtained is labeled as C-9, from which 20-40 mesh catalyst particles are tested for their activity in the microreactor. Tables 1-3 show the composition of the sample, the crystallinity before and after aging, and the activity of this model catalyst tested in the microreactor.

Example 10

18.6 g of $(NH_4)_2HPO_4$ is dissolved in 250 g of distilled water. 100 g of β molecular sieve sample is added to the solution under stirring, and pH value is adjusted to 3. The mixture is stirred and allowed to react at reaction temperature of 160° C. under reaction pressure of 0.8 MPa for 60 min, followed by filtering and drying, and then calcined at 450° C. for 6 h. The molecular sieve sample thus obtained is labeled as Pβ-2.

1.46 g of $AgNO_3$ is dissolved in 300 g of distilled water. The molecular sieve Pβ-2 is added to the silver-containing solution. The mixture is stirred and allowed to react in dark place at reaction temperature of 20° C. for 200 min, followed by filtering and drying, and then calcined at 500° C. for 2 h, so as to obtain a double-component modified molecular sieve APβ-2. Subsequently, kaolin (45%), alumina gel (15%) and APβ-2 (40%) are added into distilled water in fixed proportion under slurrying, dried at 120° C. and calcined at 500° C. for 1 h, followed by crushing and screening. The catalyst sample thus obtained is labeled as C-10, from which 20-40 mesh catalyst particles are tested for their activity in the microreactor. Tables 1-3 show the composition of the sample, the crystallinity before and after aging, and the activity of this model catalyst tested in the microreactor.

Example 11

18.6 g of $(NH_4)_2HPO_4$ and 16.2 g of $NH_4H_2PO_4$ are dissolved in 400 g of distilled water. 100 g of β molecular sieve sample is added to the solution under stirring, and pH value is adjusted to 5. The mixture is stirred and allowed to react at reaction temperature of 100° C. under reaction pressure of 0.2 MPa for 180 min, followed by filtering and drying, and then calcined at 600° C. for 2 h. The molecular sieve sample thus obtained is labeled as Pβ-3.

1.09 g of AgAc and 1.07 g of $AgNO_3$ are dissolved in 350 g of distilled water. The molecular sieve Pβ-3 is added to the silver-containing solution. The mixture is stirred and allowed to react in dark place at reaction temperature of 20° C. for 90 min, followed by filtering and drying, and then calcined at 500° C. for 2 h, so as to obtain a double-component modified molecular sieve APβ-3. Subsequently, kaolin (45%), alumina gel (15%) and APβ-3 (40%) are added into distilled water in fixed proportion under slurrying, dried at 120° C. and calcined at 500° C. for 1 h, followed by crushing and screening. The catalyst sample thus obtained is labeled as C-11, from which 20-40 mesh catalyst particles are tested for their activity in the microreactor. Tables 1-3 show the composition of the sample, the crystallinity before and after aging, and the activity of this model catalyst tested in the microreactor.

Comparative Example 1

18.6 g of $(NH_4)_2HPO_4$ is dissolved in 400 g of distilled water. 100 g of ZSM-5 molecular sieve is added to the solution under stirring, and pH value is adjusted to 3. The mixture is stirred and allowed to react at reaction temperature of 90° C. for 120 min, followed by filtering and drying, and then calcined at 550° C. for 4 h. The molecular sieve sample thus obtained is labeled as PZD-1.

1.46 g of $AgNO_3$ is dissolved in 350 g of distilled water. The molecular sieve PZD-1 is added to the silver-containing solution. The mixture is stirred and allowed to react in dark place at reaction temperature of 40° C. for 100 min, followed by filtering and drying, and then calcined at 500° C. for 2 h, so as to obtain a double-component modified molecular sieve APZD-1. Subsequently, kaolin, alumina gel and APZD-1 (40%) are added into distilled water in fixed proportion under slurrying, dried at 120° C. and calcined at 450° C. for 1 h, followed by crushing and screening. The catalyst sample thus obtained is labeled as CD-1, from which 20-40 mesh catalyst particles are tested for their activity in the microreactor. Tables 1-3 show the composition of the sample, the crystallinity before and after aging, and the activity of this model catalyst tested in the microreactor.

Comparative Example 2

18.6 g of $(NH_4)_2HPO_4$ is dissolved in 400 g of distilled water. 100 g of ZSM-5 molecular sieve is added to the solution under stirring, and pH value is adjusted to 3. The mixture is stirred and allowed to react at reaction temperature of 20° C. under reaction pressure of 0.4 MPa for 120 min, followed by filtering and drying, and then calcined at 550° C. for 4 h. The molecular sieve sample thus obtained is labeled as PZD-2.

2.19 g of $AgNO_3$ is dissolved in 400 g of distilled water. The molecular sieve PZD-2 is added to the silver-containing solution. The mixture is stirred and allowed to react in dark place at reaction temperature of 40° C. for 100 min, followed by filtering and drying, and then calcined at 500° C. for 2 h, so as to obtain a double-component modified molecular sieve APZD-2. Subsequently, kaolin (45%), alumina gel (15%) and APZD-2 (40%) are added into distilled water in fixed proportion under slurrying, dried at 120° C. and calcined at 450° C. for 1 h, followed by crushing and screening. The catalyst sample thus obtained is labeled as CD-2, from which 20-40 mesh catalyst particles are tested for their activity in the microreactor. Tables 1-3 show the composition of the sample, the crystallinity before and after aging, and the activity of this model catalyst tested in the microreactor.

Comparative Example 3

18.6 g of $(NH_4)_2HPO_4$ and 100 g of ZSM-5 molecular sieve are mechanically mixed until homogeneous and then calcined at 550° C. for 4 h. The molecular sieve sample thus obtained is labeled as PZD-3.

2.19 g of $AgNO_3$ is dissolved in 400 g of distilled water. The molecular sieve PZD-3 is added to the silver-containing solution. The mixture is stirred and allowed to react in dark place at reaction temperature of 40° C. for 100 min, followed by filtering and drying, and then calcined at 500° C. for 2 h, so as to obtain a double-component modified molecular sieve APZD-3. Subsequently, kaolin (45%), alumina gel (15%) and APZD-3 (40%) are added into distilled water in fixed proportion under slurrying, dried at 120° C. and calcined at 450° C. for 1 h, followed by crushing and screening. The catalyst sample thus obtained is labeled as CD-3, from which 20-40 mesh catalyst particles are tested for their activity in the microreactor. Tables 1-3 show the composition of the sample, the crystallinity before and after aging, and the activity of this model catalyst tested in the microreactor.

Comparative Example 4

9.3 g of $(NH_4)_2HPO_4$ is dissolved in 110 g of distilled water. 100 g of ZSM-5 molecular sieve sample is added to the solution and impregnated for 300 min, followed by drying, and then calcined at 500° C. for 4 h. The molecular sieve sample thus obtained is labeled as PZD-4.

1.46 g of $AgNO_3$ is dissolved in 350 g of distilled water. The molecular sieve PZD-4 is added to the silver-containing solution. The mixture is stirred and allowed to react in dark place at reaction temperature of 40° C. for 200 min, followed by filtering and drying, and then calcined at 500° C. for 2 h, so as to obtain a double-component modified molecular sieve APZD-4. Subsequently, kaolin (45%), alumina gel (15%) and APZD-4 (40%) are added into distilled water in abovementioned proportion under slurrying, dried at 120° C. and calcined at 450° C. for 1 h, followed by crushing and screening. The catalyst sample thus obtained is labeled as CD-4, from which 20-40 mesh catalyst particles are tested for their activity in the microreactor. Tables 1-3 show the composition of the sample, the crystallinity before and after aging, and the activity of this model catalyst tested in the microreactor.

Comparative Example 5

18.6 g of $NH_4H_2PO_4$ is dissolved in 400 g of distilled water. 100 g of β molecular sieve sample is added to the solution under stirring, and pH value is adjusted to 2. The mixture is stirred and allowed to react at reaction temperature of 50° C. for 60 min, followed by filtering and drying, and then calcined at 600° C. for 2 h. The molecular sieve sample thus obtained is labeled as PβD-1.

2.19 g of $AgNO_3$ is dissolved in 350 g of distilled water. The molecular sieve PβD-1 is added to the silver-containing solution. The mixture is stirred and allowed to react in dark place at reaction temperature of 40° C. for 100 min, followed by filtering and drying, and then calcined at 500° C. for 2 h, so as to obtain a double-component modified molecular sieve APβD-1. Subsequently, kaolin (45%), alumina gel (15%) and APβD-1 (40%) are added into distilled water in fixed proportion under slurrying, dried at 120° C. and calcined at 500° C. for 1 h, followed by crushing and screening. The catalyst sample thus obtained is labeled as CD-5, from which 20-40 mesh catalyst particles are tested for their activity in the microreactor. Tables 1-3 show the composition of the sample, the crystallinity before and after aging, and the activity of this model catalyst tested in the microreactor.

Comparative Example 6

18.6 g of $(NH_4)_2HPO_4$ is dissolved in 400 g of distilled water. 100 g of ZSM-5 molecular sieve sample is added to the solution under stirring and then 10 ml solution containing 1.46 g of $AgNO_3$ is added, and pH value is adjusted to 3. The mixture is stirred and allowed to react at reaction temperature of 120° C. under reaction pressure of 0.4 MPa for 120 min, followed by filtering and drying, and then calcined at 550° C. for 4 h. The molecular sieve sample thus obtained is labeled as APZD-5.

Subsequently, kaolin (45%), alumina gel (15%) and APZD-5 (40%) are added into distilled water in fixed proportion under slurrying, dried at 120° C. and calcined at 450° C. for 1 h, followed by crushing and screening. The catalyst sample thus obtained is labeled as CD-6, from which 20-40 mesh catalyst particles are tested for their activity in the microreactor. Tables 1-3 show the composition of the sample, the crystallinity before and after aging, and the activity of this model catalyst tested in the microreactor.

INDUSTRIAL UTILITY

The present invention provides the optimal modified molecular sieve that is obtained by the modification method in accordance with the present invention: said molecular sieve contains, based on dry basis, 88-99 wt % of a molecular sieve with a silica to alumina ratio of 15-60, 0.5-10 wt % of phosphorus based on oxide and 0.01-2 wt % of silver based on oxide.

It can be seen according to the data in Table 1 and 2 that the molecular sieves modified by the modification method of Examples 1-11 have higher relative crystallinity than the molecular sieves modified by other methods after 17 h of hydrothermal treatment. Meanwhile, it can also be seen according to the data in Table 3 that the molecular sieve model catalysts modified by the modification method of Examples 1-11 have higher activity in the microreactor than the molecular sieve catalysts modified by other methods.

TABLE 1

Hydrothermal stability of phosphorus-modified molecular sieves

| | | Relative Crystallinity (%) | | |
|---|---|---|---|---|
| Sample Ref. | $P_2O_5$ (wt %) | Before hydrothermal treatment | After 17 h of hydrothermal treatment | *Crystallinity reservation (%) |
| PZ-1 | 1.9 | 93 | 79 | 84.9 |
| PZ-2 | 2.4 | 91 | 80 | 87.9 |
| PZ-3 | 3.2 | 90 | 82 | 91.1 |
| PZ-4 | 2.8 | 91 | 82 | 90.1 |
| PZ-5 | 2.5 | 91 | 83 | 91.2 |
| PZ-6 | 2.9 | 90 | 83 | 92.2 |
| PZ-7 | 2.4 | 91 | 82 | 90.1 |
| PZ-8 | 2.8 | 92 | 81 | 88.0 |
| Pβ-1 | 1.6 | 95 | 86 | 90.5 |
| Pβ-2 | 2.0 | 94 | 88 | 93.6 |
| Pβ-3 | 2.6 | 92 | 87 | 94.6 |
| PZD-1 | 1.5 | 92 | 78 | 84.8 |
| PZD-2 | 1.0 | 92 | 77 | 83.7 |
| PZD-3 | 9.7 | 84 | 69 | 82.1 |
| PZD-4 | 4.8 | 87 | 70 | 80.4 |
| PβD-1 | 1.0 | 96 | 80 | 83.3 |

*Crystallinity reservation = relative crystallinity after hydrothermal treatment/relative crystallinity before hydrothermal treatment × 100%

TABLE 2

Hydrothermal stability of double-component modified molecular sieves

| | | | Relative Crystallinity (%) | | |
|---|---|---|---|---|---|
| Sample Ref. | $P_2O_5$ (wt %) | $Ag_2O$ (wt %) | Before hydrothermal treatment | After 17 h of hydrothermal treatment | *Crystallinity reservation (%) |
| APZ-1 | 1.8 | 0.4 | 92 | 82 | 89.1 |
| APZ-2 | 2.2 | 0.8 | 91 | 84 | 92.3 |
| APZ-3 | 2.8 | 1.1 | 88 | 83 | 94.3 |
| APZ-4 | 2.5 | 0.6 | 91 | 84 | 92.3 |
| APZ-5 | 2.1 | 0.7 | 92 | 85 | 92.4 |
| APZ-6 | 2.6 | 1.0 | 89 | 84 | 94.4 |
| APZ-7 | 2.0 | 0.7 | 90 | 84 | 93.3 |
| APZ-8 | 2.5 | 0.9 | 88 | 81 | 92.0 |
| APβ-1 | 1.6 | 0.3 | 93 | 88 | 94.6 |
| APβ-2 | 1.9 | 0.7 | 91 | 87 | 95.6 |
| APβ-3 | 2.5 | 0.9 | 88 | 84 | 95.5 |
| APZD-1 | 0.2 | 0.8 | 97 | 81 | 83.5 |
| APZD-2 | 0.3 | 1.3 | 94 | 78 | 83.0 |
| APZD-3 | 9.7 | 1.4 | 82 | 65 | 79.3 |
| APZD-4 | 0.2 | 0.9 | 95 | 80 | 84.2 |
| APZD-5 | 0.4 | 0.9 | 95 | 79 | 83.2 |
| APβD-1 | 0.3 | 1.2 | 96 | 82 | 85.4 |

*Crystallinity reservation = relative crystallinity after hydrothermal treatment/relative crystallinity before hydrothermal treatment × 100%

TABLE 3

Activity performance of modified molecular sieve model catalysts in the microreactor

| Sample Ref. | Activity performance (%, 4 h of hydrothermal aging at 800° C.) | Activity performance (%, 17 h of hydrothermal aging at 800° C.) |
|---|---|---|
| C-1 | 42 | 41 |
| C-2 | 42 | 41 |
| C-3 | 44 | 42 |
| C-4 | 43 | 42 |
| C-5 | 42 | 40 |
| C-6 | 46 | 44 |
| C-7 | 43 | 41 |
| C-8 | 43 | 40 |
| C-9 | 46 | 44 |
| C-10 | 47 | 46 |
| C-11 | 46 | 46 |
| CD-1 | 35 | 29 |
| CD-2 | 34 | 28 |
| CD-3 | 35 | 28 |
| CD-4 | 36 | 30 |
| CD-5 | 25 | 24 |

According to the above research, it has been found that the introduction of phosphorus inhibits the dealuminification of the ZSM-5 zeolite framework under hydrothermal condition and significantly improves the reservation of acid on the zeolite, so as to increase the catalytic activity and selectivity thereof. Meanwhile, in order to further substantially increase the hydrothermal stability of the molecular sieve and adjust the surface acidity of the zeolite at the same time, it is necessary to introduce the second modifying element for its modification. When the silver ion, a transition metal, is introduced into the ZSM-5 molecular sieve, its oxidation effect facilitates the formation of carbocations, which results in improved reactivity by enabling the reaction to be initiated more readily. Because the adsorption of olefins to silver is relatively weak with respect to other transition metals, the hydrogen transfer reactions may be reduced, which is favorable to increase the olefin yields. Moreover, silver can accept or donate electrons during the reaction as the transition metal and produce free radicals, which further crack into olefins, that is, its oxidationreduction effect enables the reaction to proceed according to free radical reaction mechanism, and thus the yields of light olefins may be increased.

The advantage of the present invention lies in the fact that this method is able to prevent the phosphorus constituent from being heavily washed away when the phosphorus-modified molecular sieve is modified by ion exchange with transition metals, and the double-component modified molecular sieve obtained by such modification and the model catalyst thereof have excellent hydrothermal stability and catalytic activity.

What we claim is:

1. A method for preparing double-component modified molecular sieves with improved hydrothermal stability, wherein, according to said method, the molecular sieve is added to an aqueous solution containing phosphorus and allowed to react at pH of 2-7 at a reaction temperature of 90-160° C. under a reaction pressure of 0.2-0.8 MPa for 10-200 minutes, followed by filtering, drying and calcining, so as to obtain a phosphorus-modified molecular sieve; the phosphorus-modified molecular sieve is added into an aqueous solution containing silver ions and allowed to react at a reaction temperature of 0-100° C. for 30-150 minutes, followed by filtering, drying and calcining, so as to obtain a double-component modified molecular sieve, wherein the molecular sieve is one of ZSM type or β type, molecular sieve, and the silica to alumina ratio of the molecular sieve is in the range of 15-60, the weight ratio of the aqueous solution containing silver ions to the molecular sieve is in the range from 3:1 to 7:1, and the aqueous solution containing silver ions has a concentration of 0.01-0.1 mol/L wherein the aqueous solution containing phosphorus is a solution of phosphoric acid, a solution of phosphorous acid, an aqueous solution of a soluble phosphate and/or an aqueous solution of a soluble phosphite, wherein, the soluble phosphate is one or more selected from triammonium phosphate, diammonium hydrogen phosphate, and ammonium dihydrogen phosphate, wherein the aqueous solution containing silver ions is an aqueous solution of silver nitrate, an aqueous solution of silver acetate or both wherein the aqueous solution containing phosphorus has a concentration of 0.05-1.0 mol/L.

* * * * *